(12) United States Patent
Kimura et al.

(10) Patent No.: US 6,498,245 B2
(45) Date of Patent: Dec. 24, 2002

(54) NUCLEIC ACID-IMMOBILIZED SUBSTRATE

(75) Inventors: Naoki Kimura, Chiba (JP); Namiko Shiohata, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 09/725,593

(22) Filed: Nov. 29, 2000

(65) Prior Publication Data

US 2001/0003649 A1 Jun. 14, 2001

(30) Foreign Application Priority Data

Nov. 29, 1999 (JP) ............................. 11-337433

(51) Int. Cl.[7] ................ C07H 21/00; C07H 21/02; C07H 21/04; C12Q 1/68
(52) U.S. Cl. ............... 536/25.3; 435/6; 536/25.32; 536/26.6
(58) Field of Search ................ 435/6; 536/26.6, 536/25.3, 25.32

(56) References Cited

U.S. PATENT DOCUMENTS

| | | | |
|---|---|---|---|
| 4,806,631 A | * 2/1989 | Carico et al. | ........... 536/27 |
| 5,478,893 A | 12/1995 | Ghosh et al. | |
| 5,981,734 A | 11/1999 | Mirzabekov et al. | |
| 6,048,695 A | * 4/2000 | Bradley et al. | ........... 435/6 |

FOREIGN PATENT DOCUMENTS

| | | |
|---|---|---|
| EP | 0 710 666 A1 | 5/1996 |
| WO | WO 95/35505 | 12/1995 |
| WO | WO 97/10365 | 3/1997 |
| WO | WO 98/55593 | 12/1998 |
| WO | WO 99/20640 | 4/1999 |

OTHER PUBLICATIONS

Macdougall, Allan J., "Immobilization of DNA for Affinity Chromatography and Drug–Binding Studies", Biochem. J., vol. 191, No. 3, pp. 855–858 (1980).

* cited by examiner

Primary Examiner—Jezia Riley
(74) Attorney, Agent, or Firm—Kilpatrick Stockton LLp

(57) ABSTRACT

By immobilizing identical or different nucleic acids in a plurality of dot-like areas on a carrier which comprises a base material and compound carried on the base material, the compound having one or more alkylating groups, through intermediary of the alkylating group, a nucleic acid-immobilized substrate on which nucleic acids are firmly immobilized in fine dot area without reference to chain length of nucleic acids is provided, which enables efficiently introducing the nucleic acids onto the base material in a simple manner and can be produced with a simple apparatus.

8 Claims, No Drawings

NUCLEIC ACID-IMMOBILIZED SUBSTRATE

BACKGROUND OF THE INVENTION

1. Field of the Invention

The present invention relates to a nucleic acid-immobilized substrate. More particularly, it relates to a nucleic acid-immobilized substrate that can efficiently immobilize nucleic acids on a carrier in a simple manner as well as a production method therefor and an analysis method by utilizing it.

2. Description of the Related Art

As the method for producing nucleic acid-immobilized substrates comprising a carrier on which nucleic acids and so forth are immobilized, which are used for DNA tips and so forth, the following two kinds of methods are mainly used:

(1) a method of immobilizing nucleic acids by physical adsorption using a base material coated with poly-L-lysine etc. as a carrier (International Patent Publication in Japanese (Kohyo) No. 10-503841/1998), and (2) a method of synthesizing DNA on a base material (WO97/10365).

Among the aforementioned methods, however, the method described in International Patent Publication in Japanese No. 10-503841/1998 has a drawback that if hybridization is performed by using this method, nucleic acids are dropped off from the substrate especially during operational steps, and consequently detection sensitivity may be reduced and results may be varied to cause bad reproducibility. Furthermore, this method also suffers from a drawback that a short chain nucleic acid of about 50-mer or less such as oligomers cannot be efficiently immobilized, although a long chain nucleic acid can be immobilized by this method.

Further, the method described in WO97/10365 requires an extremely special apparatus and extremely special regents, because DNA is synthesized on a base material. Thus, it is not a method that can be easily performed by anyone. Moreover, it also suffers from a drawback that nucleic acids that can be synthesized are limited to those of about 25-mer or shorter.

SUMMARY OF THE INVENTION

The present invention was accomplished in view of the aforementioned problems, and its object is to provide a nucleic acid-immobilized substrate on which nucleic acids are firmly immobilized in fine dot areas without reference to chain length of the nucleic acids, which enables efficiently introducing the nucleic acids onto a base material in a simple manner and can be produced with a simple apparatus.

The inventors of the present invention found that if nucleic acids are immobilized on a carrier that comprises a base material carrying compound having one or more alkylating groups through the intermediary of the alkylating group, the nucleic acids can firmly be immobilized on the carrier in fine dot areas without reference to chain length of the nucleic acids, and the aforementioned object can be achieved. Thus, they accomplished the present invention.

That is, the present invention provides the followings.

(1) A nucleic acid-immobilized substrate having a carrier and identical or different nucleic acids, wherein the carrier comprises a base material and compound on the base material, the compound having one or more alkylating groups, and the nucleic acids are immobilized in a plurality of dot-like areas on the carrier through the intermediary of the alkylating group.

(2) The nucleic acid-immobilized substrate according to (1), wherein the compound having the alkylating groups consists of nitrogen yperite.

(3) The nucleic acid-immobilized substrate according to (1) or (2), wherein the carrier has a structure represented by the following general formula (I):

$$M-R_n-G \qquad (I)$$

[In the formula, M represents the compound having one or more alkylating groups;

R represents a functional group selected from the group consisting of —NH—, —CH$_2$—, —NHCO—, —CONH—, —O—, —S—, —N(R$^1$)— (R$^1$ represents a normal, cyclic, or branched saturated aliphatic hydrocarbon group having 1–20 carbon atoms or unsaturated aliphatic hydrocarbon group having 1–20 carbon atoms),

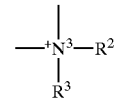

(R$^2$ and R$^3$ independently represent a hydrogen atom, a normal or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substituents; provided that one of R$^2$ and R$^3$ represents a hydrogen atom, the other represents a normal or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substituents; R$^2$ and R$^3$ may be also bonded together to form a nitrogen-containing heterocyclic group that may contain an oxygen atom), —COO—, —OCO—, —NHSO$_2$—, —NHC(S)NH— and —SO$_2$NH—;

n represents an integer of 0–20;

when two or more groups of R exist, they may be identical to or different from each other;

G represents the base material or a polymer that can be adhered to the base material].

(4) A carrier for immobilizing nucleic acids, which comprises a base material and compound carried on the base material, the compound having one or more alkylating groups.

(5) A method for producing a carrier for immobilizing nucleic acids, the carrier comprising a base material and compound carried on the base material, the compound having one or more alkylating groups, which comprises the step of getting the compound having two or more alkylating groups or the compound having one or more alkylating groups and one or more functional groups that are not alkylating groups, to covalently bond with functional groups on a surface of the base material having the functional groups can be covalently bonded with the alkylating groups or with the functional groups that are not alkylating groups, while leaving at least one of the alkylating groups of the compound.

(6) A method for producing a nucleic acid-immobilized substrate, which comprises the step of bringing nucleic acids into contact with a carrier for immobilizing nucleic acids, wherein the carrier comprises a base material and compound carried on the base material, the compound having one or more alkylating groups.

(7) A method for detecting a nucleic acid by hybridization using a nucleic acid labeled with a labeling substance, wherein the nucleic acid-immobilized substrate according to any one of (1) to (3) is used.

DETAILED DESCRIPTION OF THE PREFERRED EMBODIMENTS

Hereafter, embodiments of the present invention will be explained in detail.

<1> Carrier

The carrier used for the nucleic acid-immobilized substrate of the present invention is for immobilizing nucleic acids, and comprises a base material and compound carried on the base material, the compound having one or more alkylating groups (this may also be referred to as "alkylating reagent" hereafter).

(1) Base material

The base material used for the present invention serves as a support of the aforementioned carrier, and it is not particularly limited so long as it basically composed of a material that is insoluble in a solvent and is in a state of solid or gel at an ordinary temperature or within a temperature range around it (0–100° C.). The definition that the base material is insoluble in a solvent means that the base material is substantially insoluble in various aqueous and organic solvents used for process steps where the alkylating reagent is provided on the base material to be carried on the base material as described hereinafter, then nucleic acids are immobilized thereon as the carrier, and then the substrate is used as a DNA tip or the like.

Specific examples of the material of the carrier base material include plastics, inorganic polymers, metals, natural polymers, ceramics and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, fluorinated polyethylene, polyimide, acrylic resin and so forth. Specific examples of the inorganic polymers include glass, crystal, carbon, silica gel, graphite and so forth. Specific examples of the metals include gold, platinum, silver, copper, iron, aluminum, magnet, paramagnet, apatite and so forth. Examples of the natural polymers include cellulose, chitin, chitosan, alginic acid, derivatives thereof and so forth. Specific examples of the ceramics include alumina, silica, silicon carbide, silicon nitride, boron carbide and so forth.

The aforementioned base material may be in the form of, for example, a film, plate, fiber or the like, and its size is not particularly limited.

(2) Compound having one or more alkylating groups

The alkylating group used for the present invention refers to a group that introduces an alkyl group into another compound through a substitution reaction or addition reaction. The compound having such one or more alkylating groups is one used as an alkylating reagent, and examples thereof include alkyl halide, dialkyl sulfate, aromatic sulfonic acid alkyl ester, alkyl metal compound and so forth.

As such an alkylating reagent, nitrogen yperites can be preferably used. Nitrogen yperites can be produced by the methods disclosed in U.S. Pat. Nos. 2,141,090, 5,273,991, 5,387,707 and so forth.

Specific examples of the nitrogen yperites include halogenated alkyl-N-alkylaminobenzene, dihalogenated alkyl-N-aminobenzene, halogenated alkoxy-N-alkylaminobenzene, dihalogenated alkoxy-N-aminobenzene, halogenated alkyl-N-alkoxyaminobenzene, halogenated alkoxy-N-alkoxyaminobenzene, halogenated alkylphenylaminobenzene, halogenated alkoxy-N-sulfonylalkylbenzene, halogenated alkyl-N-sulfonylalkoxyaminobenzene, halogenated alkyl-N-carboxyalkylaminobenzene, halogenated alkoxy-N-carboxyalkylaminobenzene, halogenated alkoxy-N-carboxyalkoxyaminobenzene and so forth.

The aforementioned nitrogen yperites may have another functional group or atom as a substituent, so that they can covalently bond with the base material or with a polymer compound for physically immobilizing the alkylating group to the base material. Specific examples of such a substituent include, for example, functional groups such as hydroxyl group, halogen atom, halogenated alkyl group, halogenated acyl group, halogenated allyl group, acyl group, allyl group, carboxyl group, sulfoxyl group, phosphonium group, ketone, aldehyde, isocyanate group, isothiocyanate group, carbodiimide group, thiol group and amino group.

The position of the aforementioned substituent may be any position that does not inhibit the alkylation reaction by the nitrogen yperite. Specifically, it may be at a position other than the position of the alkylating group that participates in the alkylation reaction and the position on the tertiary nitrogen atom. The substituent is preferably introduced on an aromatic ring.

(3) Carrier

The carrier for immobilizing nucleic acids used for the present invention comprises the aforementioned base material and the aforementioned alkylating reagent carried on the base material. The term "carry" used for the present invention means that the alkylating reagent is not substantially dropped off from the base material in various solvents such as water-soluble solvents and organic solvents used when the nucleic acids are immobilized on the carrier, when the nucleic acid-immobilized substrate is used as a DNA tip etc, or the like.

As for the carrier used for the present invention, the aforementioned alkylating reagent may be carried simply by utilizing physical adhesion, or may be chemically carried through covalent bond, so long as it is carried on the aforementioned base material. However, in the carrier used for the present invention, the alkylating reagent is preferably carried on the base material through covalent bond.

Further, the alkylating reagent may be carried on the whole surface of the base material or on a part thereof, as required.

When the aforementioned alkylating reagent is carried on the base material by physical adhesion, compound comprising a polymer compound and the alkylating reagent bonded with the polymer compound through covalent bond can be used, which may also be referred to as "alkylating reagent carrying polymer compound" hereafter. Although the alkylating reagent carrying polymer compound is not particularly limited so long as it is compound comprising the alkylating reagent bonded with the polymer compound, the alkylating reagent carrying polymer compound preferably has a molecular weight in the range of 500 to 1,000,000.

The alkylating reagent carrying polymer compound carried on the base material by physical adhesion preferably has 2 to 2000 alkylating reagent molecules in the polymer molecule irrespective of the type thereof. If the number of the alkylating reagent molecules in which the alkykating reagent carrying polymer compound has, is less than 2, i.e., 1, it lacks the ability to immobilize nucleic acids. To the contrary, the number of the alkylating reagent molecules is too mach larger than the aforementioned range, its viscosity may become to high or it may not be made into a solution, and thus its handling property may be degraded when it is applied to the base material, although it may not show unsatisfactory performance as a product.

Such an alkylating reagent carrying polymer compound shows high adhesion to the aforementioned base material, and it is carried on the base material by this adhesion. A typical form of the alkylating reagent carrying polymer compound carried on the base material by physical adhesion is a coated film.

The method for obtaining the aforementioned alkylating reagent carrying polymer compound carried on the base material in the form of a coated film may be a known method, for example, spraying, immersing, brushing, stamping, vapor deposition, coating by using a film coater and so forth.

Now, the carrier carrying the alkylating reagent through covalent bond will be explained.

The alkylating reagent to be carried through covalent bond may be any one of the aforementioned ones. The alkylating reagent which the carrier has on the base material through covalent bond, preferably has 3 to 300 alkylating groups in the molecule. If the number of the alkylating groups is 3 to 300, sufficient ability to immobilize nucleic acids can be obtained, and its solution may have an appropriate viscosity and thus preferred in view of handling thereof.

To obtain a carrier carrying the aforementioned compound having the alkylating group(s) through covalent bond on the surface of the base material, which may also be referred to as "covalent bond type carrier" hereafter, for example, an alkylating reagent having one ore more alkylating groups for immobilizing nucleic acids when it is used in a carrier and further having one or more functional groups for forming covalent bond with the base material surface can be covalently bonded with functional groups of the base material having, on its surface, functional groups that can be covalently bonded with the functional groups of the alkylating reagent by a suitable method.

More specifically, the covalent bond type carrier can be obtained by, for example, getting compound having two or more alkylating groups, or compound having one or more alkylating groups and one or more functional groups that are not alkylating groups, to covalently bond with the functional groups on the surface of the base material having functional groups that can be covalently bonded with the alkylating groups or with the functional groups that are not alkylating groups, while leaving at least one of the alkylating groups of the compound.

As the compound having two or more alkylating groups or the compound having one or more alkylating groups and one or more functional groups that are not alkylating groups used for the production of the carrier that can be covalently bonded with the alkylating reagent, there can be specifically mentioned compound having two or more alkylating groups and compound having one or more alkylating groups and one or more functional groups that are not alkylating groups among the alkylating reagents mentioned in the above (2). Further, it is also possible to utilize compound consisting of any one of the alkylating reagents mentioned in the above (2) introduced with the aforementioned functional groups for providing the covalent bond by a suitable method for the production of the aforementioned covalent bond type carrier. Furthermore, it is also possible to utilize compound consisting of any one of the alkylating reagents mentioned in the above (2) further introduced with the alkylating groups as the functional groups for providing the covalent bond for the production of the aforementioned covalent bond type carrier. The method for introducing such the functional groups into the alkylating reagent may be a conventionally known method.

The position at which the functional group for providing the covalent bond is introduced is not particularly limited, so long as the alkylation reaction by the alkylation regent is not inhibited. However, the functional group is preferably introduced on an aromatic ring, when the aforementioned alkylating reagent is a nitrogen yperite.

As the base material having on its surface functional groups that can be covalently bonded with the alkylating groups or with the functional groups that are not the alkylating groups, which is possessed by the aforementioned compound, there can be mentioned, for example, the base material explained in the above (1) introduced with the functional groups that can provide covalent bond on its surface. The functional group to be introduced is not particularly limited so long as it is a functional group that can be covalently bonded with the alkylating reagent or a functional group that can be covalently bonded with the functional group other than the alkylating group. Specific examples thereof include hydroxyl group, imino group, amino group, carboxyl group, carbodiimide group, aldehyde group and so forth. These functional groups can suitably be selected depending on the functional groups of the aforementioned alkylating reagent, which forms covalent bond, and introduced onto the base material surface.

As for the method for introducing such functional groups onto the base material surface, a suitable method can be selected depending on the material of the base material, the functional group to be introduced and so forth. Furthermore, the functional group may be introduced onto the whole surface of the base material or onto a part thereof.

When amino groups are introduced onto the whole surface of a glass base material, for example, the glass base material can be immersed in a solution prepared by dissolving an amino-substituted organoalkoxysilane such as 3-aminopropyltriethoxysilane in a suitable solvent for about 2 to 3 hours under a temperature condition of 70 to 80° C. Then, the base material may be taken out from the solution, washed with water to remove the solution, and dried by heating at about 100–120° C. for about 4 to 5 hours. Further, it is also possible to allow the amino group of the aforementioned 3-aminopropyltriethoxysilane and the functional group other than the alkylating group of the alkylating reagent to react with each other using a suitable solvent so that the alkylating reagent should be directly introduced onto the surface of the glass base material.

As also for the cases where functional groups other than amino group are introduced onto a glass substrate or where functional groups are introduced onto a substrate made of a material other than glass, it is a commonly used conventional technique that various functional groups are introduced onto surfaces of the various materials mentioned in the above explanation of the base material, and methods therefor are known. Therefore, also in such cases, functional groups can be introduced onto the surface of base material by using such known methods.

Furthermore, the base materials mentioned in the above (1) include those plastic base materials that already have such functional groups as mentioned above on the base material surfaces. In such a case, those materials can be used as they are for the production of the aforementioned covalent bond type carrier without introducing the functional groups onto the base material surfaces. Further, such plastic base materials may also be used for the production of the carrier after functional groups are further introduced onto them.

In order to produce the covalent bond type carrier used for the present invention, compound having two or more alkylating groups or compound having one or more alkylating groups and one or more functional groups that are not alkylating groups, and a base material having on its surface functional groups that can be covalently bonded with the alkylating groups or with the functional groups that are not alkylating groups, are allowed to react under a suitable condition, so that the compound should be covalently bonded with the functional groups on the surface of the base material, while leaving at least one alkylating group of the compound. That is, when the compound is compound having one or more alkylating groups and one or more functional groups that are not alkylating groups, the reaction can be performed under such a condition that the functional groups that are not alkylating groups should form covalent bond. Further, when compound having only the alkylating groups is used, the reaction can be performed under such a condition that all of the alkylating groups should not form covalent bond.

The carrier for immobilizing nucleic acids obtained as described above, which comprises the base material and the compound having alkylating groups carried on the base material, can firmly immobilize nucleic acids of various kinds and sizes by utilizing the reactivity of the alkylating groups of the compound having alkylating groups.

Specifically, the carrier used for the nucleic acid-immobilized substrate of the present invention preferably has a structure represented by the following general formula (i):

$$M\text{-}R_n\text{-}G \qquad (i)$$

In the formula (i), M represents the aforementioned compound having the alkylating group, and actually a group having covalent bond portion for bonding with the aforementioned base material or polymer compound. As described above, the covalent bond is preferably present on an aromatic ring, when the compound having an alkylating group is a nitrogen yperite.

R represents a divalent functional group selected from —NH—, —CH$_2$—, —NHCO—, —CONH—, —O—, —S—, —N(R$^1$)— (R$^1$ represents a normal, cyclic, or branched saturated aliphatic hydrocarbon group having 1–20 carbon atoms or unsaturated aliphatic hydrocarbon group having 1–20 carbon atoms),

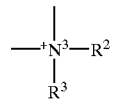

(R$^2$ and R$^3$ independently represent a hydrogen atom, a normal or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substituents. However, if one of R$^2$ and R$^3$ represents a hydrogen atom, the other represents a normal or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substituents. Alternatively, R$^2$ and R$^3$ may be bonded together to form a nitrogen-containing heterocyclic group that may contain an oxygen atom), —COO—, —OCO—, —NHSO$_2$—, —NHC(S)NH—, —SO$_2$NH— and so forth. n represents an integer of 0–20. When R consists of two or more groups, they may be identical to or different from each other.

R is a group formed as a result of covalent bond between an alkyl group or a functional group other than alkyl group of the aforementioned compound having two or more alkylating groups or having one or more alkylating groups and one or more functional groups that are not alkylating groups, and a functional group of the aforementioned base material having functional groups that can be covalently bonded with the alkylating group or with the functional group other than the alkylating group. R may contain one or more other functional groups introduced beforehand into the alkylating reagent or one or more other functional groups introduced into the base material, which are not directly involved in the aforementioned covalent bond.

G represents the base material or the polymer compound. When the aforementioned alkylating reagent is carried on the base material through physical adhesion, G represents the polymer compound, and this polymer compound is adhered to the base material to form a carrier.

<2> Nucleic acid-immobilized substrate

In the nucleic acid-immobilized substrate of the present invention, identical or different nucleic acids are immobilized in a plurality of dot-like areas on the carrier that comprises the base material and the alkylating reagent carried on the base material through the intermediary of the alkylating group.

In the nucleic acid-immobilized substrate of the present invention, the definition that nucleic acids are immobilized on dot-like areas means that the areas on which the nucleic acids are immobilized are sufficiently smaller than the size of the carrier in such a degree that a plurality of the nucleic acid-immobilized sites can be provided. The shape of the dots is not particularly limited, and arbitrarily selected depending on the way of use, purpose of use and so forth of the nucleic acid-immobilized substrate.

The dot-like nucleic acid immobilized sites of the nucleic acid-immobilized substrate of the present invention are specifically, for example, those having an approximately circular shape and having a diameter of 10–3000 μm. As for the size of the dots, the diameter is more preferably about 50–2000 μm, further preferably about 100–1500 μm. The term "approximately circular shape" means that the shape is not limited to a round but includes shapes analogous to a circle such as oval shapes without any particular limitation. The diameter of oval shape, for example, means an average value of the major axis and the minor axis.

As for the size of the dots mentioned above, if the diameter is less than 10 μm, detection may become difficult, whereas if the diameter exceeds 3000 μm, it may become difficult to secure a moderate number of dots per unit area. Therefore, if it takes into consideration ease of detection, provision of desired number of the dots per unit area and so forth, it is preferable to make the size of the dots within the aforementioned range.

The number of the dot-like nucleic acid-immobilized sites of the nucleic acid-immobilized substrate of the present invention is not particularly limited, and suitably selected depending on the way of use, purpose of use and so forth of the nucleic acid-immobilized substrate. However, for example, the number of the nucleic acid-immobilized sites may be, specifically, about 10–10000, preferably about 50–350, per 1 cm$^2$ of the nucleic acid-immobilized substrate. The geometrical arrangement of the dot-like nucleic acid-immobilized sites of the nucleic acid-immobilized substrate of the present invention may also be suitably selected depending on the way of use, purpose of use and so forth of the nucleic acid-immobilized substrate.

As the nucleic acids to be immobilized on the nucleic acid-immobilized substrate of the present invention, there can be mentioned natural DNA or synthesized DNA (including oligo nucleotides) and RNA (including oligo nucleotides) without any particular limitation. The nucleic acids to be immobilized may be single-stranded or double stranded. According to the present invention, nucleic acids that have a functional group showing reactivity with the alkylating group, are usually used as the aforementioned nucleic acids. The nucleic acids immobilized in dot-like areas of the nucleic acid-immobilized substrate of the present invention may be identical or different from each other. When different nucleic acids are used, geometrical arrangement of those nucleic acids and so forth may suitably be selected depending on the way of use, purpose of use and so forth of the nucleic acid-immobilized substrate to be obtained.

To immobilize such nucleic acids in dot-like shapes on the carrier, small amounts of nucleic acids can be provided in dot-like shape of a desired size on portions of the base material that carries the alkylating reagent under a suitable condition so that the alkylating reagent and the nucleic acids should be brought into contact with each other to cause the reaction between them. As a result of the reaction of the alkylating group of the alkylating reagent carried on the base material, and amino group, imino group or the like of the nucleic acids, the nucleic acids are covalently bonded with the alkylating reagent. If thiol groups are introduced into the nucleic acids beforehand, covalent bond is also formed by reaction of the aforementioned alkylating group and the thiol group. As a result, the nucleic acids are immobilized on the carrier.

Specifically, nucleic acids are usually provided in a state that they are contained in water or buffer so that the activity of the nucleic acids to be immobilized should be maintained during the contact and the reaction of the both. In general, the temperature for the contact is preferably 0–100° C. so that the activity of the nucleic acids to be immobilized should not be lost.

Means for providing small amounts of nucleic acids, usually in the form of water or buffer containing the nucleic acids, in dot-like areas on the carrier includes method of utilizing a dispenser, method of utilizing a pin, method of utilizing bubble jet and so forth. However, the present invention is not limited to these. Apparatuses for providing solutions in small amounts by the above methods are commercially available, and they can be used for the present invention.

When analysis is carried out by using the nucleic acid-immobilized substrate of the present invention, the nucleic acid-immobilized substrate is frequently brought into contact with nucleic acids other than the aforementioned immobilized nucleic acids and so forth. Therefore, in order to prevent nucleic acids other than the immobilized nucleic acids and so forth from non-specifically bonding with unreacted alkylating groups of the alkylating reagent carried on the carrier, after the nucleic acids are immobilized in dot-like areas on the carrier as described above, free alkylating groups are preferably blocked by bringing them into contact with an excessive amount of bovine serum albumin (BSA), casein, salmon sperm DNA or the like.

In the nucleic acid-immobilized substrate of the present invention obtained as described above, the nucleic acids are very firmly carried on the carrier, and they are not released even by washing methods widely used for hybridization and so forth (washing methods using surface active agents). If analysis is carried out by using the nucleic acid-immobilized substrate, the analysis can be performed with superior reproducibility and quantification ability. Further, since the nucleic acid-immobilized substrate of the present invention can immobilize nucleic acids without reference to the number and length of the chains, various nucleic acids can be simultaneously dealt with on the same substrate. Based on these, the nucleic acid-immobilized substrate of the present invention can be used as a DNA tip and so forth for techniques of determining nucleotide sequences by hybridization using a large number of nucleic acids, for example, SBH (Sequencing by Hybridization) method, SHOM (Sequencing by Hybridization with Oligonucleotide Matrix) method and so forth with superior performance.

EXAMPLES

Hereafter, the present invention will be explained with reference to the following examples.

<Preparation Example>
(1) Preparation of alkylating reagent

Hydroxyethylmethylaniline (20 g) was gradually added to phosphorus oxychloride (22.3 g) at 45° C., and stirred at 90° C. for 1 hour. The reaction mixture was cooled to 0° C., then gradually added with a mixture (87.3 g) of N-methylformanilide, phosphorus oxychloride and benzene (1:1:0.5), and stirred at 35° C. for 3 hours. This reaction mixture was cooled with addition of ice, neutralized with addition of 4 N sodium hydroxide, and then extracted with benzene. The extract was concentrated and purified by silica gel chromatography (developing solvent: toluene) to obtain p-N-chloroethyl-N-methylaminobenzaldehyde. The NMR spectrum data thereof are shown below.

[NMR spectrum data]
$^1$H-NMR (CDCl$_3$): $\delta$=3.10 (s, 3H), 67 =3.65 (m, 2H), $\delta$=3.75 (m, 2H), $\delta$=6.70 (d, 2H), $\delta$=7.75 (d, 2H), $\delta$=9.75 (s, 1H)

(2) Production of aminated slide glass

A 10% (v/v) solution of 3-aminopropyltriethoxysilane in ethanol (20 ml) was added to distilled water (180 ml) and stirred sufficiently. The mixture was adjusted to pH 3 to 4 with addition of 6 N HCl, and 15 pieces of slide glass were immersed in the mixture and heat-treated at 75° C. for 2 hours. After the completion of the heat treatment, the slide glass pieces were pulled up from the solution, sufficiently rinsed with distilled water, and heat-treated at 115° C. for 4 hours to obtain aminated slide glass.

<Example>
(1) Preparation of alkylating reagent carrying slide glass

The alkylating reagent (1.25 g) obtained in the above Preparation Example(B) was dissolved in methanol (25 ml), gradually added with sodium borohydride cyanide and stirred. Then, 5 pieces of the aminated slide glass obtained in the aforementioned Preparation Example(2) were immersed in the solution, and the solution was stirred at room temperature for 18 hours. These slide glass pieces were immersed in methanol (500 ml) and the methanol was stirred at room temperature for 30 minutes. Further, they were dried at 37° C. for 30 minutes to obtain alkylating reagent carrying slide glass.

(2) Immobilization of nucleic acid on alkylating reagent carrying slide glass

An oligonucleotide having the nucleotide sequence shown in SEQ ID NO: 1 (21-mer) was dissolved in 2 M NaCl at a concentration of 100 ng/μl to obtain a DNA solution. By using SPBIO (Hitachi Software Engineering Co., Ltd.), the DNA solution was spotted on 500 areas at predetermined positions on the alkylating reagent carrying slide glass obtained in the above (1). This was put into a drier and dried at 37° C. for 15 minutes. Then, the slide glass was immersed in Buffer A (0.2 M sodium chloride, 0.1 M Tris-HCl (pH 7.5), 0.05% Triton X-100) containing 3% BSA (bovine serum albumin) and dried at 37° C. for 15 minutes. Subsequently, the slide was washed with TE buffer (10 mM Tris-HCl (pH 7.2), 1 mM EDTA) and dried at 37° C. for 15 minutes to obtain alkylating reagent-immobilized slide glass on which the double-stranded DNA was immobilized.

(3) Hybridization

As a probe used for hybridization detection, used was an oligonucleotide having a nucleotide sequence complementary to the nucleotide sequence of aforementioned SEQ ID NO: 1, which was labeled with biotin.

On the DNA-immobilized portions of the aforementioned slide glass, a hybridization solution [3×SSC (SSC: 1.5 M NaCl, 0.15 M sodium citrate), 10% dextran, 1 pmol of biotinylated probe], 30 μl each, was placed, and heated overnight on a water bath at 42° C.

(4) Post-hybridization

After the hybridization, the hybridization solution was lightly soaked up from the slide glass, and the slide glass was subjected to post-hybridization washing under the following condition to remove non-specifically adsorbed probe.

[Post-hybridization washing solution and condition]

First step: 2×SSC, 1% SDS; room temperature, 5 minutes, 2 times

Second step: 0.2×SSC, 1% SDS; 40° C., 5 minutes, 2 times

Third step: 2×SSC; room temperature, 5 minutes, once (5) Detection of hybridization The slide glass after the aforementioned post-hybridization washing was blocked by immersing it in Buffer A (500 ml) containing 3% BSA at room temperature for 30 minutes. Then, it was immersed in 45 ml of a solution of streptavidin-alkaline phosphatase conjugate (Gibco BRL, prepared by diluting 2000 times the stock solution with Buffer A containing 3% BSA) and allowed to react at room temperature for 30 minutes. Then, the slide glass was immersed in Buffer A (50 ml) and left at room temperature for 5 minutes. This procedure was repeated twice to remove the conjugate not bound to the biotin.

Then, the slide glass was washed once with Buffer B (30 ml). Finally, it was immersed in a substrate solution (20 ml of Buffer B, 18 μl of 5-bromo-4-chloro-3-indolyl phosphate (BCIP) solution, 36 μl of nitroblue tetrazolium (NBT) solution) and left at room temperature for 3 hours to perform the color development reaction. The results are shown in Table 1.

[Composition of Buffer A]

0.2 M NaCl 0.1 M Tris-HCl (pH 7.5)

0.05% Triton X-100

[Composition of Buffer B]

0.1 M NaCl 0.1 M Tris-HCl (pH 9.5)

<Comparative Example>

(1) Immobilization of nucleic acid on poly-L-lysine-coated slide glass

An oligonucleotide having the nucleotide sequence shown in SEQ ID NO: 1 (21-mer) was dissolved in 0.2×SSC at a concentration of 100 ng/μl to obtain a DNA solution. By using SPBIO (Hitachi Software Engineering Co., Ltd.), the DNA solution was spotted on 500 areas at predetermined positions on poly-L-lysine-coated slide glass (Sigma). This was put into a chamber and allowed to react at room temperature for 2 hours. Subsequently, it was dried at 80° C. in a vacuum drier for 2 hours. The slide glass was washed with 0.1% SDS, then immersed in a blocking solution (1 g of succinic anhydride, 100 ml of N-methylpyrrolidone, 100 ml of 0.2 M sodium borate (pH 8.0)) at room temperature for 10 minutes, and washed 4 times with distilled water to obtain poly-L-lysine-coated slide glass on which the nucleic acid was immobilized.

(2) Hybridization

Hybridization was performed in the same manner as in Example(2) except that the poly-L-lysine-coated slide glass prepared in Comparative Example(1) was used instead of the alkylating reagent carrying slide glass.

(3) Post-hybridization

The slide glass was treated in the same manner as in Example(3) except that the poly-L-lysine-coated slide glass prepared in Comparative Example(2) was used instead of the alkylating reagent carrying slide glass.

(4) Detection of hybridization

Hybridization was detected in the same manner as in Example(4) except that the poly-L-lysine-coated slide glass prepared in Comparative Example(3) was used instead of the alkylating reagent carrying slide glass.

TABLE 1

| | Signal Detection |
|---|---|
| Example | ○ |
| Comparative Example | X |

○: Signal appeared uniformly and clearly.
Δ: A part of signal appeared unevenly or unclearly.
X: Most part of signal appeared unevenly or unclearly.

From the results shown in Table 1, it can be seen that, according to the method for detecting nucleic acid of the present invention, detection of nucleic acids appears as a clear signal with high sensitivity.

According to the present invention, there is provided a nucleic acid-immobilized substrate on which DNA is stably immobilized. Since the substrate of the present invention can immobilize nucleic acids without suffering from limitations of number or size of chains thereof, various nucleic acids can be simultaneously dealt with on the same base material. Furthermore, since the substrate of the present invention is stable for light, heat, moisture in air and so forth, it shows superior storability.

Moreover, since the nucleic acids are firmly bonded with the carrier through covalent bond, it can be a nucleic acid-immobilized substrate effective in use as a DNA tip or the like excellent in reproducibility and quantification ability.

This invention being thus described, it will be obvious that the same may be varied in various ways. Such variations are not to be regarded as departure from the spirit and scope of the invention, and all such modifications would be obvious for one skilled in the art intended to be included within the scope of the following claims.

What is claimed is:

1. A nucleic acid-immobilized substrate having a carrier and identical or different nucleic acids, wherein the carrier comprises a base material and compound carried on the base material, wherein the compound having two or more alkylating groups, or the compound having one or more alkylating groups material at first and functional groups that are not alkylating groups, is carried on the base and one or more then the nucleic acids are immobilized in a plurality of dot-like areas on the carrier through the intermediary of covalent bonds between the nucleic acid and the alkylating group.

2. A nucleic acid-immobilized substrate having a carrier and identical or different nucleic acids, wherein the carrier comprises a base material and compound carried on the base material, the compound being nitrogen yperite, and the nucleic acids are immobilized in a plurality of dot-like areas on the carrier through the intermediary of covalent bonds between the nucleic acid and the nitrogen yperite.

3. The nucleic acid-immobilized substrate according to claim 1, wherein carrier has a structure represented by the following general formula (I):

$$M—R_n—G \qquad (I)$$

wherein M represents the compound having one or more alkylating groups;

R represents a functional group selected from the group consisting of —NH—, —CH$_2$—, —NHCO—, —CONH—, —O—, —S—, N(R$^1$)—, wherein R1 represents a linear, cyclic, or branched saturated aliphatic hydrocarbon group having 1–20 carbon atoms or unsaturated aliphatic hydrocarbon group having 1–20 carbon atoms,

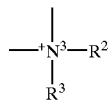

Wherein R$^2$ and R$^3$ independently represent a hydrogen atom, a linear or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substituents; provided that one of R2 and R3 represents a hydrogen atom, the other represents a linear or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substitutents; R2 and R3 may be also bonded together to form a nitrogen-containing heterocyclic group that may contain an oxygen atom, —COO—, —OCO—, NHSO2—. —NHC(S)NH— and —SO2NH—; n represents an integer of 0–20; when two or more groups of R exist, they may be identical to or different from each other; G represents the base material or a polymer adhering to the base material.

4. A carrier for immobilizing nucleic acids, which comprises a base material and compound carried on the base material, wherein the compound has two or more alkylating groups, or has one or more alkylating groups and one or more functional groups that are not alkylating groups.

5. A method for producing a carrier for immobilizing nucleic acids, the carrier comprising a base material and compound carried on the base material, the compound having one or more alkylating groups, which comprises the step of getting the compound having two or more alkylating groups, or the compound having one or more alkylating groups and one or more functional groups that are not alkylating groups, to covalently bond with functional groups on a surface of the base material having the functional groups that can be covalently bonded with the alkylating groups or with the functional groups that are not alkylating groups, while leaving at least one of the alkylating groups of the compound.

6. A method for producing a nucleic acid-immobilized substrate, which comprises the step of bringing nucleic acids into contact with a carrier for immobilizing nucleic acids, wherein the carrier comprises a base material and compound carried on the base material, the compound having one or more alkylating groups.

7. A method for detecting a nucleic acid by hybridization using a nucleic acid labeled with a labeling substance.

wherein the nucleic acid-immobilized substrate according to any one of claims 1 to 3 is used.

8. The nucleic acid-immobilized substrate according to claim 1, wherein carrier has a structure represented by the following general formula (I):

$$M—R_n—G \qquad (I)$$

wherein M represents the compound having one or more alkylating groups;

R represents a functional group selected from the group consisting of —NH—, —CH$_2$—, —NHCO—, —CONH—, —O—, —S—, N(R$^1$)—, wherein R1 represents a linear, cyclic, or branched saturated aliphatic hydrocarbon group having 1–20 carbon atoms or unsaturated aliphatic hydrocarbon group having 1–20 carbon atoms,

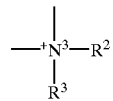

Wherein $R^2$ and $R^3$ independently represent a hydrogen atom, a linear or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substituents; provided that one of R2 and R3 represents a hydrogen atom, the other represents a linear or branched saturated aliphatic hydrocarbon group having 1–20 carbon atoms or unsaturated aliphatic hydrocarbon group having 1–20 carbon atoms, a cycloalkyl group, an aryl group or an aralkyl group, which may have one or more substitutents; R2 and R3 may be also bonded together to form a nitrogen-containing heterocyclic group that may contain an oxygen atom, —COO—, —OCO—, NHSO2—. —NHC(S)NH— and —SO2NH—; n represents an integer of 0–20; when two or more groups of R exist , they may be identical to or different from each other; G represents the base material or a polymer adhering to the base material.

* * * * *

UNITED STATES PATENT AND TRADEMARK OFFICE
CERTIFICATE OF CORRECTION

PATENT NO. : 6,498,245 B2
DATED : December 24, 2002
INVENTOR(S) : Naoki Kimura and Namiko Shiohata It is certified that error appears in the above-identified patent and that said Letters Patent is hereby corrected as shown below:

Column 2,
Lines 17-22, delete "
$$-\underset{\underset{R^3}{|}}{\overset{|}{{}^+N^3}}-R^2$$
" and replace with --
$$-\underset{\underset{R^3}{|}}{\overset{|}{N^+}}-R^2$$
--.

Column 7,
Lines 45-50, delete "
$$-\underset{\underset{R^3}{|}}{\overset{|}{{}^+N^3}}-R^2$$
" and replace with --
$$-\underset{\underset{R^3}{|}}{\overset{|}{N^+}}-R^2$$
--.

Column 13,
Lines 52-57, delete "
$$-\underset{\underset{R^3}{|}}{\overset{|}{{}^+N^3}}-R^2$$
" and replace with --
$$-\underset{\underset{R^3}{|}}{\overset{|}{N^+}}-R^2$$
--.

Column 15,
Lines 3-8, delete "
$$-\underset{\underset{R^3}{|}}{\overset{|}{{}^+N^3}}-R^2$$
" and replace with --
$$-\underset{\underset{R^3}{|}}{\overset{|}{N^+}}-R^2$$
--.

Signed and Sealed this

Eighteenth Day of October, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA

<400> SEQUENCE: 1
gttacccaca taccacgaat c                                                    21